United States Patent [19]

Or et al.

[11] Patent Number: 5,780,604
[45] Date of Patent: Jul. 14, 1998

[54] 11,12-CYCLIC PHOSPHITE OR PHOSPHATE DERIVATIVES OF ERYTHROMYCIN AND RELATED MACROLIDES

[75] Inventors: Yat Sun Or, Libertyville; Richard F. Clark, Mundelein, both of Ill.; Daniel T. Chu, Santa Clara, Calif.

[73] Assignee: Abbott Laboratories, Abbott Park, Ill.

[21] Appl. No.: 938,143

[22] Filed: Sep. 26, 1997

[51] Int. Cl.$^6$ .................................................. C07H 17/08
[52] U.S. Cl. ................................... 536/7.3; 536/7.4
[58] Field of Search ................................ 536/7.3, 7.4

[56] References Cited

U.S. PATENT DOCUMENTS 4,331,803  5/1982  Watanabe et al. .

FOREIGN PATENT DOCUMENTS

| 0596802 A1 | 5/1994 | European Pat. Off. . |
| 0248279 B1 | 8/1994 | European Pat. Off. . |
| 2 697 524 | 5/1994 | France . |
| 93/21199 | 10/1993 | WIPO . |

OTHER PUBLICATIONS

Recueil. Journal of the Royal Netherlands Chem. Soc., vol. 94, No. 11 (Nov. 1975), pp. 236–238, W. Slawinski et al., "The Structure of Erythromycin A Cyclic Carbonate".

*Primary Examiner*—Michael G. Ambrose
*Attorney, Agent, or Firm*—Mona Anand

[57] ABSTRACT

Disclosed are the antibacterial compounds having the formulas:

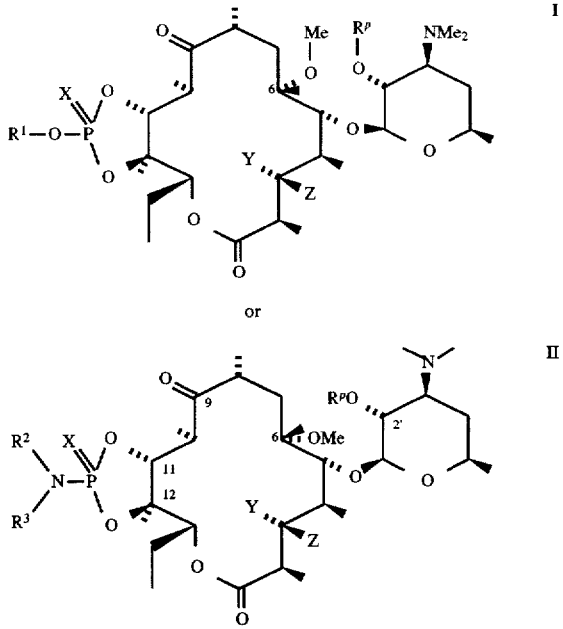

or pharmaceutically acceptable salts and esters thereof. Also disclosed are the processes for preparing compounds of formulas (I), and II) of the invention, pharmaceutical compositions comprising a therapeutically effective amount of a compound of the invention in combination with a pharmaceutically acceptable carrier, as well as a method for treating bacterial infections by administering to a mammal a pharmaceutical composition containing a therapeutically-effective amount of a compound of the invention.

13 Claims, No Drawings

11,12-CYCLIC PHOSPHITE OR PHOSPHATE DERIVATIVES OF ERYTHROMYCIN AND RELATED MACROLIDES

TECHNICAL FIELD

The present invention relates to novel semi-synthetic macrolides having antibacterial activity and useful for the treatment and prevention of bacterial infections. More particularly, the present invention relates to cyclic phosphites having antibacterial properties, compositions containing such compounds and methods for using the same, as well as processes for making such compounds.

BACKGROUND OF THE INVENTION

Erythromycins A through D, represented by formula (I),

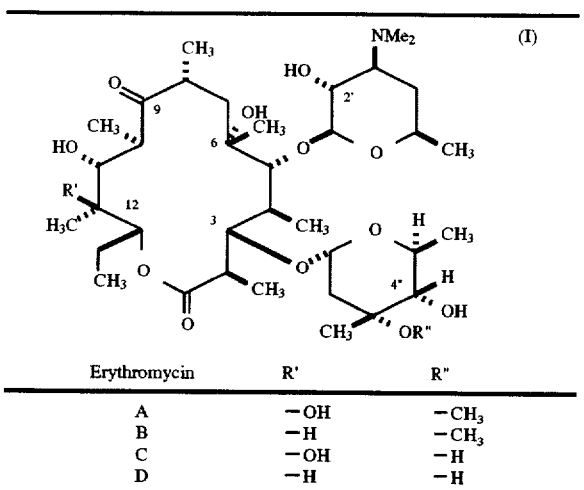

| Erythromycin | R' | R" |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

U.S. Pat. No. 4,331,803 discloses 6-O-methyl erythromycin A which exhibits a desirable antibacterial activity against many gram-positive bacteria, mycoplasmas, etc., and are clinically and widely used. However, it has only weak antimicrobial activity against gram-negative bacteria and poor acid stability.

Slowinski et al. described the preparation of erythromycin 11,12-carbonates in *Recl. Trav. Chim. Pays-Bas.* (1975) 94:236–238. Further, several patent applications have been published on the preparation of 6-O-methyl-3-descladinose-3-oxo erythromycin cyclic 11,12-carbamate derivatives (Taisho Pharm. Co. Ltd. WO9321199-A1, Roussel-Uclaf FR2697524-A1, Roussel-Uclaf EP596802-A1). In EP-A-0 248 279, Baker et al. disclose 6-O-methyl erythromycin cyclic 11,12-carbamate derivatives.

It is an object of the invention to provide novel antibiotic compounds and their nontoxic, pharmaceutically acceptable salts, a novel process for preparing the compounds and intermediates for their preparation.

SUMMARY OF THE INVENTION

In one aspect, the present invention relates to a compound having the formula:

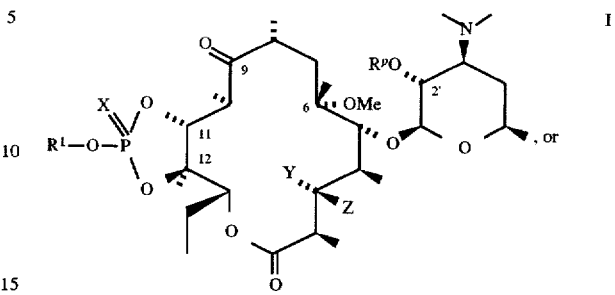

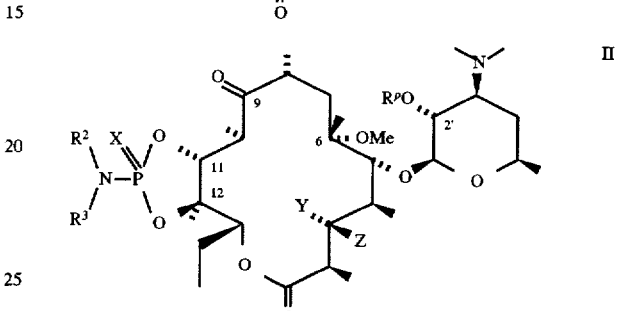

or pharmaceutically acceptable salts and esters thereof. In formulas I and II, above, R$^1$ is hydrogen, C$_1$–C$_{10}$ alkyl, C$_1$–C$_{12}$ alkenyl, or C$_1$–C$_{12}$ alkynyl, each of which may be optionally substituted with aryl, substituted aryl, heteroaryl, or substituted heteroaryl;

X is O or absent;

R$^p$ is hydrogen or hydroxy protecting group;

R$^2$ and R$^3$ are independently at each occurrence hydrogen, C$_1$–C$_{10}$ alkyl, C$_1$–C$_{12}$ alkenyl, or C$_1$–C$_{12}$ alkynyl, each of which may be optionally substituted with aryl, substituted aryl, heteroaryl, or substituted heteroaryl; or R$^2$ and R$^3$ taken together with the atom to which they are attached form a 3–10 membered heterocycloalkyl ring; and Y is hydrogen, Z is cladinose or Y and Z taken together form an oxo group.

In another aspect, the present invention relates to a process for preparing the compounds corresponding to formula I comprising the steps of:

a) reacting a compound of formula:

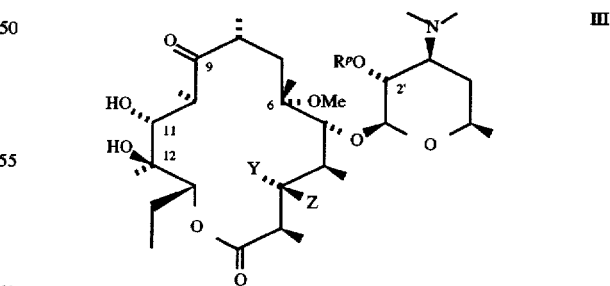

wherein:

R$^p$ is hydrogen or hydroxy protecting group;

Y is hydrogen, Z is cladinose or Y and Z taken together form an oxo group;

(a) with phosphorus trichloride and 2,6-lutidine;

(b) reacting the compound from step (a) with R$^1$-OH, wherein R$^1$ is as defined above; and (c) optionally oxidizing the compound from step (b) and deprotecting the hydroxy-protected group.

In still another aspect, the present invention relates to a process for preparing a compound of formula U, which comprises reacting the compound of formula III with phosphorous trichloride and an amine, oxidizing the resulting compound; and optionally deprotecting the hydroxy-protected group.

In yet still another aspect, the present invention relates to pharmaceutical compositions comprising a therapeutically effective amount of a compound of the invention in combination with a pharmaceutically acceptable carrier and treatment of antibacterial infections with such compositions. Suitable carriers and methods of formulation are also disclosed. The compounds and compositions of the present invention are expected to have antibacterial activity.

Still another aspect of this invention is a method for treating bacterial infections comprising administering to a mammal in need of such treatment a pharmaceutical composition containing a therapeutically-effective amount of a compound of the invention.

DETAILED DESCRIPTION OF THE INVENTION

Definitions

The terms "$C_1$–$C_{10}$-alkyl" as used herein refer to saturated, straight- or branched-chain hydrocarbon radicals containing between one and ten carbon atoms, respectively. Examples of $C_1$–$C_{10}$ alkyl radicals include methyl, ethyl, propyl and isopropyl, n-butyl, tert-butyl, neopentyl, n-hexyl, n-heptyl, octyl, and n-decyl, for example.

The term "$C_1$–$C_{12}$-alkenyl" denotes a monovalent group derived from a hydrocarbon moiety containing from two to twelve carbon atoms and having at least one carbon-carbon double bond by the removal of a single hydrogen atom. Alkenyl groups include, for example, ethenyl, propenyl, butenyl, 1-methyl-2-buten-1-yl, and the like.

The term "$C_1$–$C_{12}$-alkynyl" as used herein refers to a monovalent group derived from a hydrocarbon containing from two to twelve carbon atoms and having at least one carbon-carbon triple bond by the removal of a single hydrogen atom. Representative alkynyl groups include ethynyl, 2-propynyl (propargyl), 1-propynyl and the like.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, dichloromethane, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "aryl" as used herein refers to a mono- or bicyclic carbocyclic ring system having one or two aromatic rings including, but not limited to, phenyl, naphthyl, tetrahydronaphthyl, indanyl, indenyl and the like.

The terms "halo" and "halogen" as used herein refer to an atom selected from fluorine, chlorine, bromine and iodine.

The term "halo-$C_1$–$C_3$-alkyl" as used herein refers to a $C_1$–$C_3$-alkyl group as defined above wherein 1, 2 or 3 hydrogen atoms thereon are independently replaced by a halogen atom.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted aryl" as used herein refers to an aryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

"Hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

A the term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, New York, 1986.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl)amino, formyl, carboxy, alkoxycarbonyl, $C_1$-$C_3$-alkyl-CO—O—, $C_1$-$C_3$-alkyl-CO—NH—, or carboxamide; except that tetrafluorophenyl and pentafluorophenyl are also included within the definition of "substituted aryl."

The term "substituted heteroaryl" as used herein refers to a heteroaryl group as defined herein substituted by independent replacement of one, two or three of the hydrogen atoms thereon with Cl, Br, F, I, OH, $C_1$-$C_3$-alkyl, $C_1$-$C_6$-alkoxy, methoxymethoxy, amino, or $C_1$-$C_3$-alkyl-amino, or may also refer to a mono-oxo substituted heteroaryl compound, such as 4-oxo-1H-quinoline, for example.

The term "substituted heterocycloalkyl" as used herein, refers to a heterocycloalkyl group, as defined above, substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl-)amino, carboxaldehydo, carboxy, alkoxycarbonyl, $C_1$-$C_3$-alkyl-CO—O—, $C_1$-$C_3$-alkyl-CO—NH—, or carboxamide.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butryates, acrylates and ethylsuccinates.

Preferred Embodiments

In one embodiment of the invention is a compound having the formula (I) as described above. In one preferred embodiment is a compound of formula (I) wherein Y and Z are taken together form an oxo group. In another preferred embodiment is a compound of formula (I) wherein Y and Z are taken together form an oxo group, and X is oxygen.

In second embodiment of the invention is a compound having the formula (II) as described above. In one preferred embodiment is a compound of formula (II) wherein Y and Z are taken together form an oxo group, and X is oxygen.

Representative compounds of the invention include, but are not limited to, the following compounds:

Compound of Formula (I), wherein: $R^1$ is methyl, $R^p$ is benzoyl, X is absent, and Y and Z taken together form an oxo group;

Compound of Formula (I), wherein: $R^1$ is methyl, $R^p$ is hydrogen, X is absent, and Y and Z taken together form an oxo group;

Compound of Formula (I), wherein: $R^1$ is ethyl, $R^p$ is benzoyl, X is absent, and Y and Z taken together form an oxo group;

Compound of Formula (I), wherein: $R^1$ is ethyl, $R^p$ is hydrogen, X is absent, and Y and Z taken together form an oxo group;

Compound of formula (I), wherein $R^1$ is hydrogen, Rp is benzoyl, X=O; and Y and Z taken together form an oxo group;

Compound of formula (I), wherein $R^1$ is hydrogen, $R^p$ is benzoyl, X=O; and Y and Z taken together form an oxo group;

Compound of formula (I), wherein $R^1$ is methyl, $R^p$ is benzoyl, X=O; and Y and Z taken together form an oxo group;

Compound of formula (I), wherein $R^1$ is methyl, $R^p$ is hydrogen, X=O; and Y and Z taken together form an oxo group;

Compound of formula (II), wherein $R^p$ is benzoyl, $R^2$ and $R^3$ are each (—$CH_2CH_2$—O—$CH_2CH_2$—), X=O, and Y and Z taken together form an oxo group;

Compound of formula (II), wherein $R^p$ is hydrogen, $R^2$ and $R^3$ are each (—$CH_2CH_2$—O—$CH_2CH_2$—), X=O, and Y and Z taken together form an oxo group.

Pharmaceutical Compositions

The pharmaceutical compositions of the present invention comprise a therapeutically effective amount of a compound of the present invention formulated together with one or more pharmaceutically acceptable carriers. As used herein. the term "pharmaceutically acceptable carrier" means a non-toxic. inert solid. semi-solid or liquid filler. diluent. encapsulating material or formulation auxiliary of any type. Some examples of materials which can serve as pharmaceutically acceptable carriers are sugars such as lactose. glucose and sucrose: starches such as corn starch and potato starch: cellulose and its derivatives such as sodium carboxymethyl cellulose. ethyl cellulose and cellulose acetate; powdered tragacanth; malt: gelatin: talc: excipients such as cocoa butter and suppository waxes; oils such as peanut oil. cottonseed oil; safflower oil; sesame oil: olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline: Ringer's solution; ethyl alcohol, and phosphate buffer solutions. as well as other non-toxic compatible lubricants such as sodium lauryl sulfate and magnesium stearate. as well as coloring agents. releasing agents. coating agents. sweetening. flavoring and perfuming agents. preservatives and antioxidants can also be present in the composition. according to the judgment of the formulator. The pharmaceutical compositions of this invention can be administered to humans and other animals orally. rectally. parenterally. intracisternally. intravaginally. intraperitoneally. topically (as by powders. ointments. or drops). bucally. or as an oral or nasal spray.

Liquid dosage forms for oral administration include pharmaceutically acceptable emulsions. microemulsions. solutions. suspensions. syrups and elixirs. In addition to the active compounds. the liquid dosage forms may contain inert diluents commonly used in the art such as. for example. water or other solvents. solubilizing agents and emulsifiers such as ethyl alcohol. isopropyl alcohol. ethyl carbonate. ethyl acetate. benzyl alcohol. benzyl benzoate. propylene glycol. 1,3-butylene glycol. dimethylformamide. oils (in particular. cottonseed. groundnut. corn. germ. olive. castor. and sesame oils). glycerol. tetrahydrofurfuryl alcohol. polyethylene glycols and fatty acid esters of sorbitan. and mixtures thereof. Besides inert diluents. the oral compositions can also include adjuvants such as wetting agents. emulsifying and suspending agents. sweetening. flavoring. and perfuming agents.

Injectable preparations. for example. sterile injectable aqueous or oleaginous suspensions may be formulated according to the known art using suitable dispersing or wetting agents and suspending agents. The sterile injectable preparation may also be a sterile injectable solution. suspension or emulsion in a nontoxic parenterally acceptable diluent or solvent. for example. as a solution in 1,3-butanediol. Among the acceptable vehicles and solvents that may be employed are water. Ringer's solution. U.S.P. and isotonic sodium chloride solution. In addition. sterile. fixed oils are conventionally employed as a solvent or suspending medium. For this purpose any bland fixed oil can be employed including synthetic mono- or diglycerides. In addition. fatty acids such as oleic acid are used in the preparation of injectables.

The injectable formulations can be sterilized. for example. by filtration through a bacterial-retaining filter, or by incorporating sterilizing agents in the form of sterile solid compositions which can be dissolved or dispersed in sterile water or other sterile injectable medium prior to use.

In order to prolong the effect of a drug. it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which. in turn. may depend upon crystal size and crystalline form. Alternatively. delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed. the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter. polyethylene glycol or a suppository wax which are solid at ambient temperature but liquid at body temperature and therefore melt in the rectum or vaginal cavity and release the active compound.

Solid dosage forms for oral administration include capsules. tablets. pills. powders. and granules. In such solid dosage forms. the active compound is mixed with at least one inert. pharmaceutically acceptable excipient or carrier such as sodium citrate or dicalcium phosphate and/or a) fillers or extenders such as starches. lactose. sucrose. glucose. mannitol. and silicic acid. b) binders such as. for example. carboxymethylcellulose. alginates. gelatin. polyvinylpyrrolidinone. sucrose. and acacia. c) humectants such as glycerol. d) disintegrating agents such as agar-agar. calcium carbonate. potato or tapioca starch. alginic acid. certain silicates. and sodium carbonate. e) solution retarding agents such as paraffin. f) absorption accelerators such as quaternary ammonium compounds. g) wetting agents such as. for example. cetyl alcohol and glycerol monostearate. h) absorbents such as kaolin and bentonite clay. and i) lubricants such as talc. calcium stearate. magnesium stearate. solid polyethylene glycols. sodium lauryl sulfate. and mixtures thereof. In the case of capsules. tablets and pills. the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets. dragees. capsules. pills. and granules can be prepared with coatings and shells such as enteric coatings and other coatings well known in the pharmaceutical formulating art. They may optionally contain opacifying agents and can also be of a composition that they release the active ingredient(s) only. or preferentially. in a certain part of the intestinal tract. optionally. in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets. dragees. capsules. pills. and granules can be prepared with coatings and shells such as enteric coatings. release controlling coatings and other coatings well known in the pharmaceutical formulating art. In such solid dosage forms the active compound may be admixed with at least one inert diluent such as sucrose. lactose or starch. Such dosage forms may also comprise. as is normal practice. additional substances other than inert diluents. e.g.. tableting lubricants and other tableting aids such a magnesium stearate and microcrystalline cellulose. In the case of capsules. tablets and pills. the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: 9-BBN for 9-borabicyclo[3.3.1]nonane; AIBN for azobisisobutyronitrile; $Bu_3SnH$ for tributyltin hydride; CDI for carbonyldiimidazole; DBU for 1,8-diazabicyclo[5.4.0]undec-7-ene; DEAD for diethylazodicarboxylate; DMAP for 4-dimethylaminopyridine; DMF for dimethyl formamide; DPPA for diphenylphosphoryl azide; EtOAc for ethyl acetate; MeOH for methanol; NaHMDS for sodium hexamethyldisilazane; $NaN(TMS)_2$ for sodium bis(trimethylsilyl) amide; NMMO for N-methylmorpholine N-oxide; TEA for triethylamine; THF for tetrahydrofuran; TPP for triphenylphosphine. The compounds of the present invention are prepared by the representative methods described below.

Synthetic Methods

The compounds and processes of the present invention will be better understood in connection with the following synthetic schemes which illustrate the methods by which the compounds of the invention may be prepared.

The preparation of the compounds of the invention of formulae I, and II is outlined in reaction Schemes 1–4 below.

Scheme 1 illustrates the preparation of the starting compounds 6, the 6-O-methyl erythromycin A, for the preparation of compounds of formulae I and II of the invention. The preparation of the 6-O-substituted erythromycin A is described in U.S. Pat. Nos. 4,990,602, 4,331,803, 4,680,368, and 4,670,549, which are incorporated herein by reference. Also incorporated by reference is European Patent Application EP 260,938. The 6-O-methyl erythromycin A is known as clarithromycin and is also commercially available from Abbott Laboratories.

In general, the C-9-carbonyl group of compound 1 is protected as an oxime. (V is $=N-O-R^1$ or $=N-O-C(R^4)(R^5)-O-R^1$ where $R^1$ is defined previously and $R^4$ and $R^5$ are each independently selected from the group consisting of (a) hydrogen, (b) unsubstituted $C_1-C_{12}$-alkyl, (c) $C_1-C_{12}$-alkyl substitute with aryl, and (d) $C_1-C_{12}$-alkyl substituted with substituted aryl, or $R^7$ and $R^8$ taken together with the carbon to which they are attached form a $C_3-C_{12}$-cycloalkyl ring). An especially preferred carbonyl protecting group V is O-(1-isopropoxy-cyclohexyl) oxime.

The 2'- and 4"-hydroxy groups of 2 are protected by reaction with a suitable hydroxy protecting reagent, such as those described by T. W. Greene and P. G. M. Wuts in *Protective Groups in Organic Synthesis*, 2nd ed., John Wiley & Son, Inc., 1991, which is incorporated by reference. Hydroxy protecting groups include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of compound 2 may be accomplished sequentially or simultaneously to provide compound 3 where $R^p$ is a hydroxy protecting group. A preferred protecting group $R^1$ is trimethylsilyl.

The 6-hydroxy group of compound 3 is then methylated by reaction with a methylating agent in the presence of base to give compound 4. Methylating agents include methyl chloride, bromide, iodide or methyl sulfonate. Examples of the solvents used are aprotic solvents such as dimethylsulfoxide, diethylsulfoxide, N,N- dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like.

The deprotection of the 2'- and 4"-hydroxyl groups is then carried out according to methods described in literature, for example, by Greene and Wuts (op. cit.). The conditions used for the deprotection of the 2'- and 4"-hydroxyl groups usually results in the conversion of X to =N—OH. (For example, using acetic acid in acetonitrile and water results in the deprotection of the 2'- and 4"-hydroxyl groups and the conversion of X from =N—O—$R^1$ or =N—O—$C(R^4)(R^5)$ —O—$R^1$, where $R^1$, $R^4$ and $R^5$ are as defined previously, to =N—OH.) If this is not the case, the conversion is carried out in a separate step.

The deoximation reaction can be carried out according to the methods described in the literature, for example by Greene and Wuts (op. cit.) and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like, and inorganic nitrite salts such as sodium nitrite or potassium nitrite. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid. The amount of acid used is from about 1 to about 10 equivalents of the amount of compound 5 used. In a preferred embodiment, the deoximation is carried out using an organic acid such as formic acid in ethanol and water to give the desired product 6.

Scheme 1

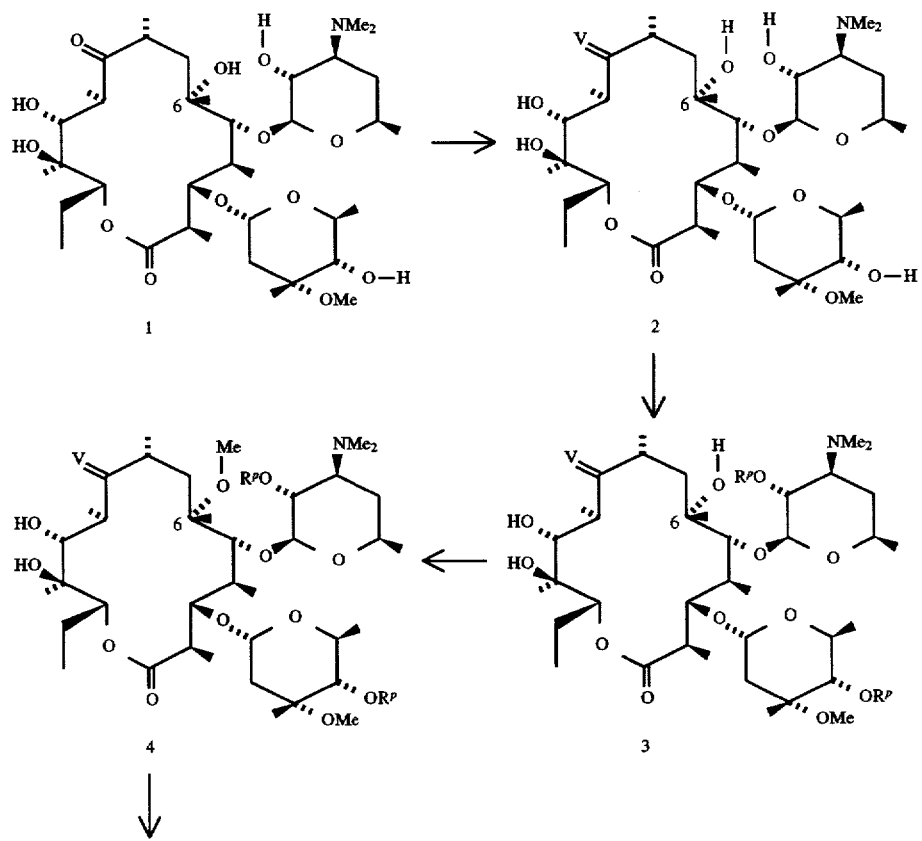

-continued
Scheme 1

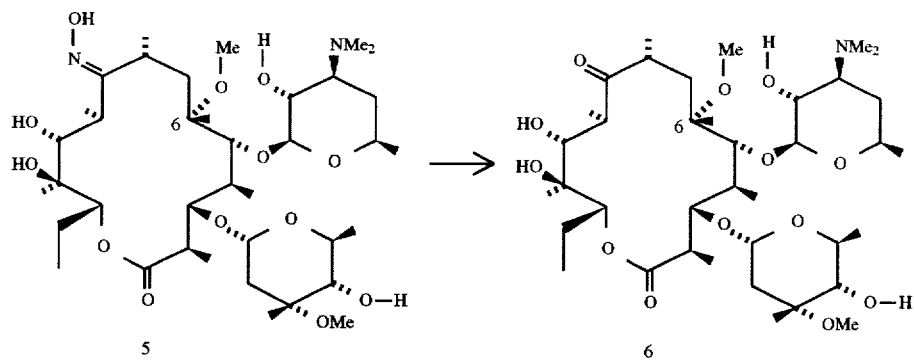

Scheme 2 illustrates the preparation of compound 9 used for the preparation of compounds of formulae I, and II, wherein Y and Z taken together is oxo. In accordance with the Scheme, the cladinose moiety of compound 6 is removed either by aqueous butanol, o-butanol and t-butanol, for example. The reaction mixture is then neutralized with an alkali metal base, the product is extracted with a suitable organic solvent such as ether, ethyl acetate or methylene chloride, for example, and Scheme 2

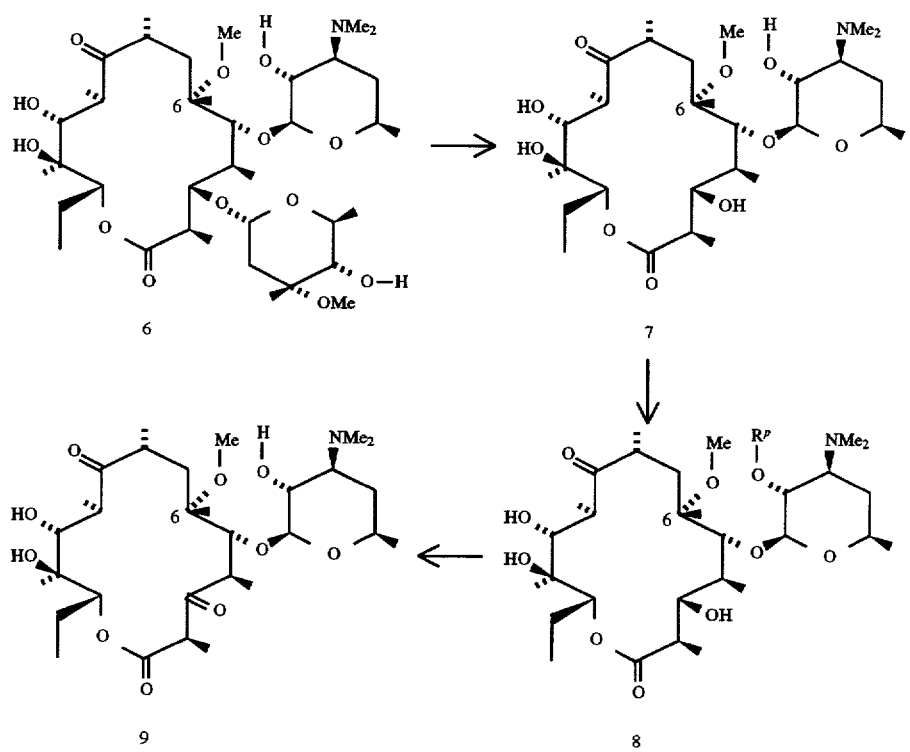

acid hydrolysis or by enzymatic hydrolysis to give compound 7. Typically, 6-O-substituted erythromycin A 6 is reacted with a dilute concentration of a strong acid at from about −10° to about 35° C. for about 0.5 to about 24 hours to remove the cladinose moiety to obtain compound 7. Suitable strong acids include, but are not limited to, hydrochloric acid, sulfuric acid, dichloroacetic acid, trichloroacetic acid, perchloric acid, chloroacetic acid, trifluoroacetic acid and the like. The reaction may be accomplished with a suspension of the reagents in aqueous alcohol, such as for example, methanol, ethanol, propanol, iso-propanol, the organic layer washed and dried. The compound is optionally isolated, but preferably is carried forward in solution.

The 2'-hydroxy group of the compound 7 is protected by reaction with a suitable hydroxy protecting reagent in an aprotic solvent, as described by T. W. Greene and P. G. M. Wuts in *Protective Groups in Organic Synthesis*, 2nd ed., John Wiley & Son, Inc., 1991, which is incorporated by reference to obtain 2'-protected compound 8. The hydroxy protecting reagents include, for example, acetic anhydride, benzoic anhydride, benzyl chloroformate, hexamethyl disilazane, or a trialkylsilyl chloride. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Preferred protecting groups are trimethylsilyl, acetyl and benzoyl. By way of example, compound 7 is treated with benzoic anhydride and triethylamine to prepare the 2'-benzoyl derivative. It is possible to reverse the order of the steps of removing the cladinose and protecting the 2'-hydroxy group without affecting the yield of the process. The 3-hydroxy group of compound 8 thus obtained can be oxidized to the keto group to obtain compound 9 using a modified Swern oxidation procedure. Suitable oxidizing agents are N-chlorosuccinimide-dimethyl sulfide or carbodiimide-dimethylsulfoxide. In a typical example, compound 8 is added into a pre-formed N-chloro-succinimide and dimethyl sulfide complex in a chlorinated solvent such as methylene chloride at −10° to 25° C. After being stirred for 0.5–4 hours, a tertiary amine such as triethylamine or Hunig's base is added to produce the corresponding ketone.

In accordance with Scheme 3A, Compound 9 is then reacted with phosphorous trichloride in presence of 2,6-lutidine and tetrahydrofuran from about 0° C. to ambient temperature for about one hour to obtain the intermediate compound 10, which is then reacted with an amine of the formula $R^2$—NH—$R^3$, wherein $R^2$ and $R^3$ are as defined above. The reaction is carried out at room temperature for about twelve hours to obtain a mixture of compounds 11A and 12A. After isolation of compounds 11A and 12A, the removal of the respective 2'-hydroxy protecting groups is carried out according to methods described in literature, for example, by T. W. Greene and P. G. M. Wuts in *Protective Groups in Organic Synthesis*, 2nd ed., John Wiley & Son, Inc., 1991, which is incorporated herein by reference, to provide compounds 11B and 12B.

Scheme 3A

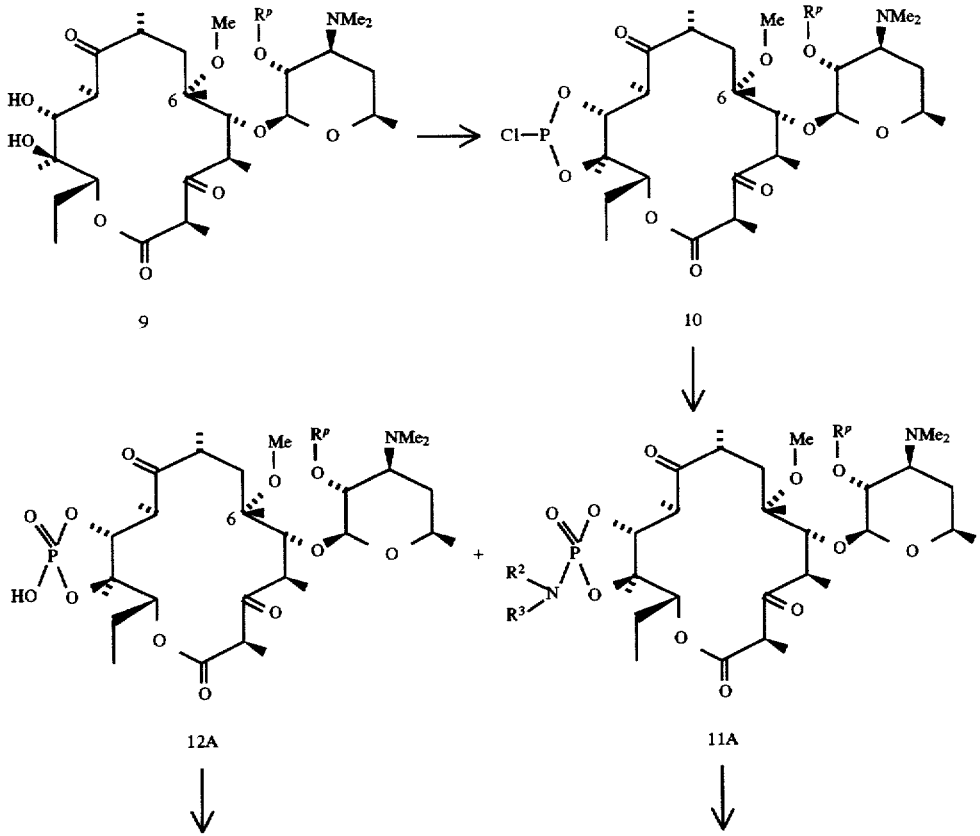

-continued
Scheme 3A

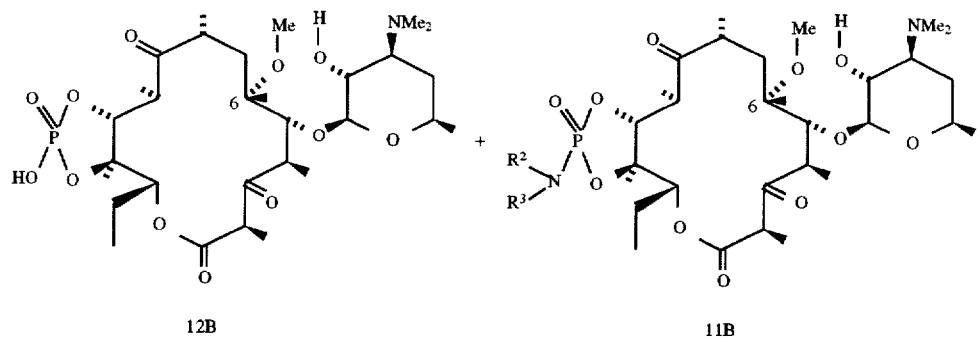

Alternatively, in accordance with Scheme 3B, compound 9 may be reacted with phosphorous trichloride in 2,6-lutidine and THF from about −0° C. to about ambient temperature for about one hour followed by reaction with an alcohol at room temperature for about 12 hours to obtain compound 13A.

Compound 13A is then oxidized with N-methylmorpholine N-oxide to obtain compound 14A. Each of compounds 13A and 14A may in turn be deprotected as described above to give 13B and 14B, respectively.

Scheme 3B

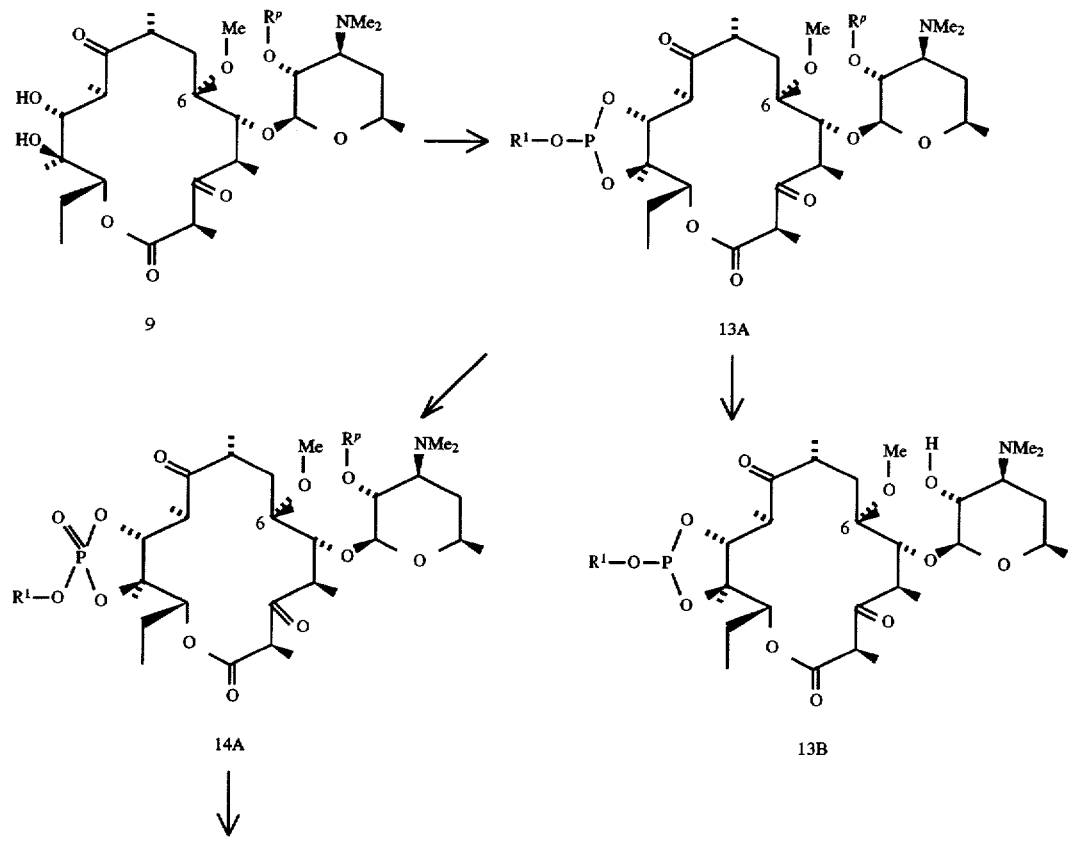

-continued
Scheme 3B

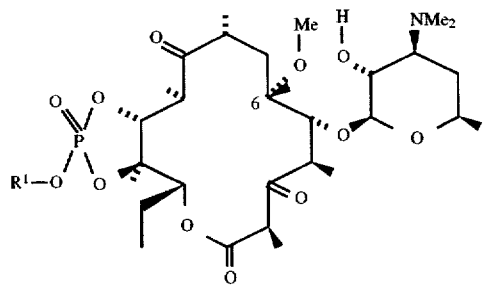

14B

Scheme 4 illustrates the preparation of the compounds of the invention 17, 18 and 19 of formulae II and I wherein Y is hydrogen and Z is cladinose. The starting compound 6 is first protected at the 2'- and 4"-hydroxy groups to obtain the corresponding bis-protected compound 15. Compound 15 is then treated with phosphorus trichloride and 2,6-lutidine in tetrahydrofuran as illustrated in Scheme 3A to obtain the intermediate compound 16 which in turn is reacted with an amine to obtain compound 17 of the invention. Alternatively, compound 16 is reacted with an $R^1$-OH to obtain compound 18 of the invention which is then oxidized by reaction with N-methylmorpholine N-oxide to afford compound 19 of the invention.

Scheme 4

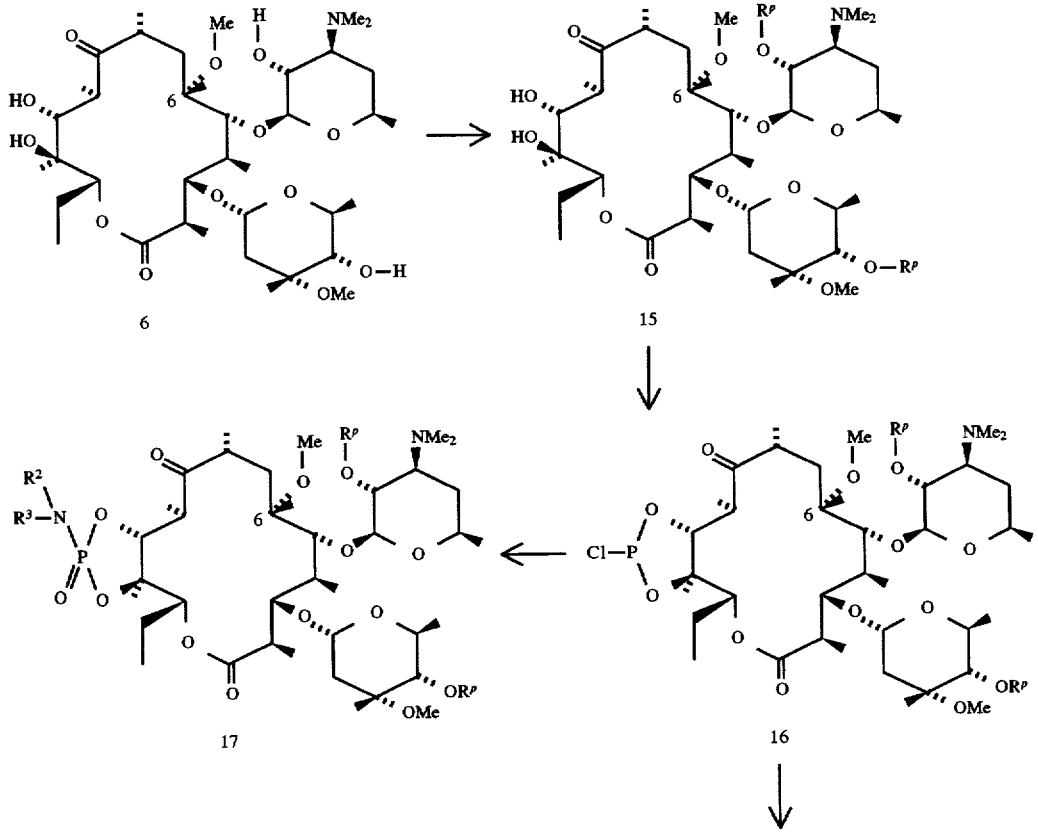

-continued
Scheme 4

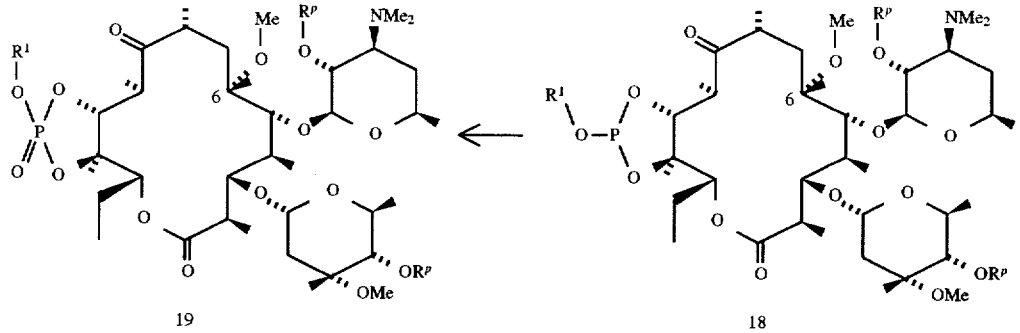

The following Examples illustrate the invention and are not limiting of the invention.

EXAMPLES

Example 1

2'-O-benzoyl-5-O-desosaminyl-3-deoxy-3-oxo-6-O-methylerythronolide A

Example 1 illustrates the preparation of compound 9 of Scheme 2, which is used as a starting material for preparation of compounds of Examples 2, 3 and 5.

Step 1a. 5-O-desosaminyl-6-O-methylerythronolide A

Compound 6 of Scheme 1, available as clarithromycin from Abbott Lab (900 g, 1.2 mole) was suspended in water (10.8L) and ethanol (4.0L), and the resulting slurry was stirred at room temperature until homogeneous (about 20 minutes). HCl (1.00M, 2.16L) was added over 15 minutes, and the reaction mixture was stirred for 20 hours. NaOH solution (2.00M, 1.20L) was added over 30 minutes until pH 10.5–11.0 was reached, and the reaction mixture was stirred for 2 hours. The precipitate was collected and washed with cold water, which was dried under vacuum at 50° C. to afford 601 g of the title compound. MS m/z (M+H)$^+$: 590.

Step 1b. 2'-O-benzoyl-5-O-desosaminyl-6-O-methylerythronolide A

To a solution of 5-O-desosaminyl-6-O-methylerythronolide A, (600 g, 1.01 mol from step 2a above) in methylene chloride (2.0L) was added 90% technical grade benzoic anhydride (380 g, 1.59 mol). Triethylamine (222 mL, 1.59 mol) was added over 10 minutes, and the thick solution was stirred for 48 hours. Sodium bicarbonate solution (10%, 1.5L) was added, and the mixture was stirred for 30 minutes. The layers were separated, and the organic fraction was washed with water (3×600 mL) and brine (600 mL). The organic layer was dried (Na$_2$SO$_4$) and filtered, and the volatiles were removed on a rotary evaporator to leave a syrup. Trituration with a warm solution of hexane (2.0L) and ethyl acetate (100 mL) converted the product to white crystals. The product was filtered, washed with hexane and dried in a vacuum oven overnight at ambient temperature to give the title compound (691 g). MS m/z (M+H)$^+$: 694.

Step 1c. 2'-O-benzoyl-5-O-desosaminyl-3-deoxy-3-oxo-6-O-methylerythronolide A

A sample of N-chlorosuccinimide (57.0 g, 0.42 mol) was slurried in anhydrous methylene chloride (600 mL), and dimethyl sulfide (36.0 mL, 0.49 mol) was added dropwise over 30 minutes. A sample of the compound from step 2b (200.0 g, 0.29 mol) was dissolved in methylene chloride (1.20L), and this solution was added to the reaction mixture over 45 minutes. After stirring for 30 minutes a solution of triethylamine (40.0 mL) in methylene chloride (200 mL) was added dropwise over 30 minutes. The resulting solution was washed with sodium bicarbonate (10%, 3×600 mL) and brine (600 mL). The organic fraction was dried (Na$_2$SO$_4$) and filtered, and the volatiles were removed on a rotary evaporator to give a thick syrup, which became a solid upon standing. The solid was crushed and dried overnight at ambient temperature in a vacuum oven to give the title compound (196 g). MS m/z (M+H)$^+$: 692.

Example 2

2a. Compound 11A from Scheme 3A: R$^2$, R$^3$ is (—CH$_2$CH$_2$—O—CH$_2$CH$_2$—), R$^p$ is benzoyl 2b. Compound 12A from Scheme 3A: R$^p$ is benzoyl To a 0° C. solution of 19 microliters phosphorous trichloride and 1 milliliter THF is added a separately prepared solution of 150 milligrams of the compound resulting from Example 1, 100 microliters 2,6-lutidine (4 equivalents), and 1 milliliter THF over 2 minutes. The mixture is stirred at 0° C. for 1.5 hours and 48 microliters (2.5 equivalents) morpholine added. The mixture is allowed to warm to ambient temperature and stirred for 16 hours. The reaction mixture is filtered through a 3 gram silica gel plug by eluting first with 35% acetone/hexanes to elute less polar amidophosphate product, 2a, (12 milligrams, 7% yield), MS m/z (M+H)$^+$: 823, and then eluting with 89:10:1 dichloromethane/methanol/ammonium hydroxide to elute more polar, phosphoric acid product, 2b, (79 milligrams, 49% yield) MS m/z (M+H)$^+$: 754

$^{13}$C NMR (CDCl$_3$) d 169.4(C-1), 51.0(C-2), 20.9(C-2Me), 204.6(C-3), 47.0(C-4), 13.9(C-4Me), 78.0(C-5), 77.7 (C-6), 19.6(C-6Me), 49.3(C-6OMe), 38.9(C-7), 44.2(C-8), 18.2(C-8Me), 215.1 (C-9), 38.9(C-10), 14.2(C-10Me), 80.5 (C-11), 82.8(C-12), 77.6(C-13), 21.8(C-14), 10.5(C-15), 101.4(C-1'), 71.8(C-2'), 63.5(C-3'), 40.7(C-3'NMe), 31.3(C-4'), 69.1(C-5'), 20.9(C-6'), 165.1 (benzoyl carbonyl carbon), 132.7,130.3,129.7,128.2 (aromatic carbons).).

Example 3

Compound 13B from Scheme 3B: R$^1$ is methyl

Example 3a, Compound 13A from Scheme 3B: R$^1$ is methyl, R$^p$ is benzoyl

To a −20° C. solution of 138 microliters (1.1 equivalents) phosphorous trichloride in 7 milliliters freshly distilled THF was added a separately prepared solution of 1 gram of the compound resulting from Example 1, 740 microliters 2,6-lutidine (4.4 equivalents) and 4 milliliters THF over 1 minute. Upon addition, the reaction was warmed to 0° C. for 10 minutes. The reaction mixture is warmed to ambient temperature and stirred for 2 hours. It is then recooled to 0° C. and 160 microliters methanol (3.5 equivalents) added over 3 minutes. The mixture is warmed to ambient temperature and stirred for 1.5 hours. The reaction mixture is loaded onto a 35 gram silica gel plug and eluted with 30:90 acetone/hexanes collecting 30 milliliter fractions to provide the methyl phosphite (486 milligrams). MS m/z $(M+H)^+$ 752
Example 3b. Compound 13B from Scheme 3B: $R^1$ is methyl, $R^p$ is H The compound resulting from Example 3a was dissolved in methanol and was heated at 65° C. for 2 hours under an inert atmosphere. After concentrating and drying to constant weight the crude product is purified on silica gel eluting with methanol/chloroform under an inert atmosphere to provide the title compound. MS m/z $(M+H)^+$: 648

Example 4

Compound 14A from Scheme 3B: $R^1$ is methyl $R^p$ is benzoyl

To a room temperature solution of 450 milligrams of the compound from Example 3a, in 4 milliliters acetone was added 62 milligrams 4-methylmorpholine N-oxide (1 equivalent). The mixture was stirred for 1 hour at ambient temperature under inert atmosphere and concentrated in vacuo. The mixture was then purified with silica gel chromatography eluting with 40:60 acetone/hexanes to provide the methyl phosphate target. MS m/z $(M+H)^+$: 768

Example 5

Compound 13B from Scheme 3B: $R^1$ is ethyl
Example 5a, Compound 13A from Scheme 3B: $R^1$ is ethyl, $R^p$ is benzoyl To a –20° C. solution of 138 microliters (1.1 equivalents) phosphorous trichloride in 7 milliliters freshly distilled THF was added a separately prepared solution of 1 gram of the compound resulting from Example 1, 740 microliters 2,6-lutidine (4.4 equivalents) and 4 milliliters THF over 1 minute. Upon addition, the reaction was warmed to 0° C. for 10 minutes. The reaction mixture is warmed to ambient temperature and stirred for 2 hours. It was then recooled to 0° C. and 160 microliters ethanol added over 3 minutes. The mixture is warmed to ambient temperature and stirred for 1.5 hours. The reaction mixture is loaded onto a 35 gram silica gel plug and eluted with 30:90 acetone/hexanes collecting 30 milliliter fractions to provide the ethyl phosphite.
Example 5b. Compound 13B from Scheme 3B: $R^1$ is ethyl, $R^p$ is H The compound resulting from Step 3a was dissolved in methanol and was heated at 65° C. for 2 hours under an inert atmosphere After concentrating and drying to constant weight the crude product is purified on silica gel eluting with methanol/chloroform under an inert atmosphere to provide the title compound. MS m/z $(M+H)^+$:662

Example 6
Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35°–37° C.

for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table I demonstrate the antibacterial activity of the compounds of the invention.

TABLE 1

Antibacterial Activity (MIC's) of Selected Compounds

| Microorganism | Ery. A standard | Example 3 | Example 5 |
|---|---|---|---|
| Staphylococcus aureus ATCC 6538P | 0.2 | 25 | 25 |
| Staphylococcus aureus A5177 | 3.1 | 25 | 25 |
| Staphylococcus aureus A-5278 | >100 | >100 | >100 |
| Staphylococcus aureus CMX 642A | 0.39 | 25 | 50 |
| Staphylococcus aureus NCTC10649M | 0.39 | 25 | 25 |
| Staphylococcus aureus CMX 553 | 0.39 | 50 | 50 |
| Staphylococcus aureus 1775 | >100 | >100 | >100 |
| Staphylococcus epidermidis 3519 | 0.39 | 25 | 25 |
| Enterococcus faecium ATCC 8043 | 0.05 | 25 | 25 |
| Streptococcus bovis A-5169 | 0.02 | 12.5 | 12.5 |
| Streptococcus agalactiae CMX 508 | 0.05 | 12.5 | 12.5 |
| Streptococcus pyogenes EES61 | 0.05 | 12.5 | 12.5 |
| Streptococcus pyogenes 930 | >100 | >100 | >100 |
| Streptococcus pyogenes PIU 2548 | 6.2 | 12.5 | 12.5 |
| Micrococcus luteus ATCC 9341 | 0.05 | 25 | 25 |
| Micrococcus luteus ATCC 4698 | 0.2 | 25 | 50 |
| Escherichia coli JUHL | >100 | >100 | >100 |
| Escherichia coli SS | 0.78 | 50 | 50 |
| Escherichia coli DC-2 | >100 | >100 | >100 |
| Candida albicans CCH 442 | >100 | >100 | >100 |
| Mycobacterium smegmatis ATCC 114 | 3.1 | 100 | 100 |
| Nocardia Asteroides ATCC9970 | 0.1 | 12.5 | 12.5 |
| Haemophilis Influenzae DILL AMP R | 4 | >128 | >128 |
| Streptococcus Pheumoniae ATCC6303 | 0.06 | | |
| Streptococcus Pheumoniae GYR 1171 | 0.06 | 8 | 4 |
| Streptococcus Pheumoniae 5979 | >128 | >128 | >128 |
| Streptococcus Pheumoniae 5649 | 16 | 16 | 16 |

We claim:

1. A compound having the formula:

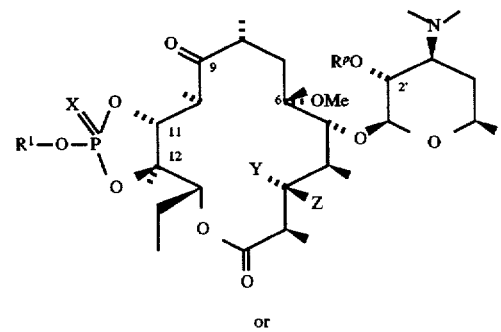

or

25

-continued

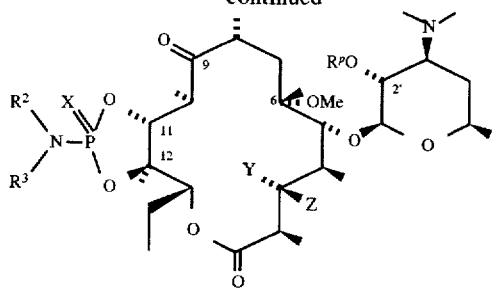

or pharmaceutically acceptable salts and esters thereof, wherein:

- $R^1$ is hydrogen, $C_1$–$C_{10}$ alkyl, $C_1$–$C_{12}$ alkenyl, or $C_1$–$C_{12}$ alkynyl, each of which may be optionally substituted with aryl, substituted aryl, heteroaryl, or substituted heteroaryl;
- X is O or absent;
- $R^P$ is hydrogen or hydroxy protecting group;
- $R^2$ and $R^3$ are hydrogen, $C_1$–$C_{10}$ alkyl, $C_1$–$C_{12}$ alkenyl, or $C_1$–$C_{12}$ alkynyl, each of which may be optionally substituted with aryl, substituted aryl, heteroaryl, or substituted heteroaryl; or $R^2$ and $R^3$ taken together with the atom to which they are attached form a 3–10 membered heterocycloalkyl ring; and
- Y is hydrogen, Z is cladinose or Y and Z taken together form an oxo group.

2. The compound according to claim 1, wherein Y is hydrogen and Z is cladinose.

3. The compound according to claim 1, wherein Y and Z take together form an oxo group.

4. A compound according to claim 3, which is selected from the group consisting of:

Compound of Formula (I), wherein: $R^1$ is methyl, $R^P$ is benzoyl, X is absent, and Y and Z taken together form an oxo group;

Compound of Formula (I), wherein: $R^1$ is methyl, $R^P$ is hydrogen, X is absent, and Y and Z taken together form an oxo group;

Compound of Formula (I), wherein: $R^1$ is ethyl, $R^P$ is benzoyl, X is absent, and Y and Z taken together form an oxo group;

Compound of Formula (I), wherein: $R^1$ is ethyl, $R^P$ is hydrogen, X is absent, and Y and Z taken together form an oxo group;

Compound of formula (I), wherein $R^1$ is hydrogen, $R^P$ is benzoyl, X=O; and Y and Z taken together form an oxo group;

Compound of formula (I), wherein $R^1$ is hydrogen, $R^P$ is hydrogen, X=O; and Y and Z taken together form an oxo group;

Compound of formula (I), wherein $R^1$ is methyl, $R^P$ is benzoyl, X=O; and Y and Z taken together form an oxo group;

Compound of formula (I), wherein $R^1$ is methyl, $R^P$ is hydrogen, X=O; and Y and Z taken together form an oxo group;

Compound of formula (II) wherein $R^P$ is benzoyl, $R^2$ and $R^3$ are each (—$CH_2CH_2$—O—$CH_2CH_2$—), X=O, and Y and Z taken together form an oxo group;

Compound of formula (II), wherein $R^P$ is hydrogen, $R^2$ and $R^3$ are each (—$CH_2CH_2$—O—$CH_2CH_2$—), X=O, and Y and Z taken together form an oxo group.

26

5. A process for preparing a compound of formula

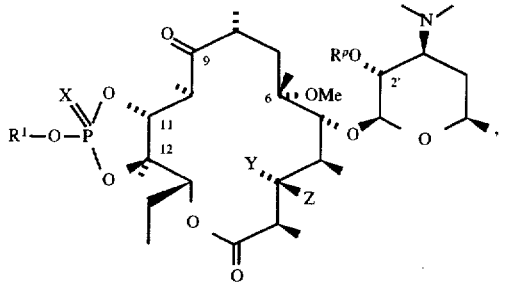

wherein:

- $R^1$ is hydrogen, $C_1$–$C_{10}$ alkyl, $C_1$–$C_{12}$ alkenyl, or $C_1$–$C_{12}$ alkynyl, each of which may be optionally substituted with aryl, substituted aryl, heteroaryl, or substituted heteroaryl;
- X is O or absent;
- $R^1$ is hydrogen or hydroxy protecting group;
- Y is hydrogen, Z is cladinose or Y and Z together form an oxo group; comprising the steps of:

(a) reacting a compound of formula:

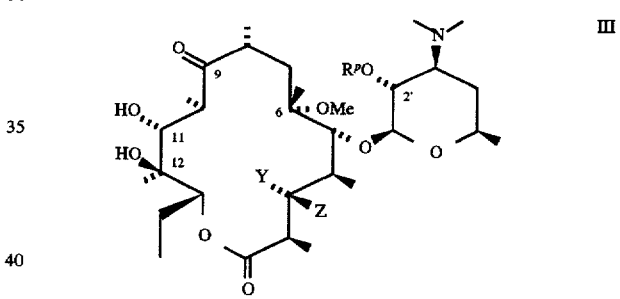

wherein:

$R^P$, Y and Z are as defined above, with phosphorus trichloride and 2,6-lutidine;

(b) reacting the compound from step (a) with $R^1$-OH, wherein $R^1$ is as defined above; and (c) optionally oxidizing the compound from step (b) and deprotecting the hydroxy-protected group.

6. The process according to claim 5, wherein Y and Z taken together form an oxo group, and X is absent.

7. The process according to claim 6, wherein $R^1$ is methyl and $R^P$ is benzoyl or hydrogen.

8. The process according to claim 6, wherein $R^1$ is ethyl and $R^P$ is benzoyl or hydrogen.

9. The process according to claim 5, wherein $R^1$ is methyl, $R^P$ is benzoyl or hydrogen, X=O and Y and Z taken together form an oxo group.

10. The process according to claim 5, wherein $R^1$ is hydrogen, $R^P$ is benzoyl or hydrogen, X=O and Y and Z taken together form an oxo group.

11. A process for preparing a compound of formula:

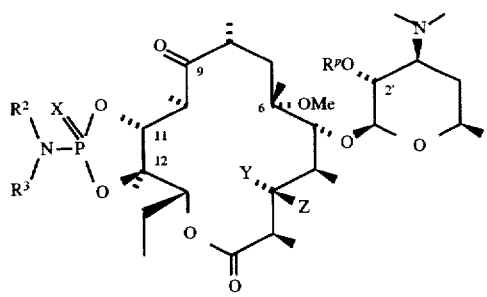

II wherein:

X is O or absent;

$R^P$ is hydrogen or hydroxy protecting group;

$R^2$ and $R^3$ are hydrogen, $C_1$–$C_{10}$ alkyl, $C_1$–$C_{12}$ alkenyl, or $C_1$–$C_{12}$ alkynyl, each of which may be optionally substituted with aryl, substituted aryl, heteroaryl, or substituted heteroaryl; or $R^2$ and $R^3$ taken together with the atom to which they are attached form a 3–10 membered heterocycloalkyl ring; and Y is hydrogen, Z is cladinose or Y and Z taken together form an oxo group; comprising the steps of:

(a) reacting a compound of the formula:

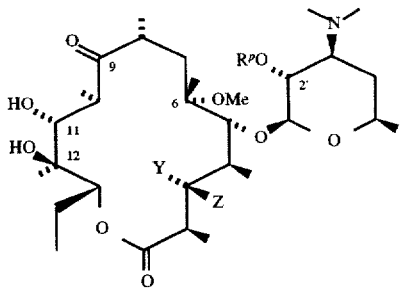

III wherein:

$R^P$, Y and Z are as defined above; with phosphorous trichloride and an amine of the formula $R^2R^3NH$, where $R^2$ and $R^3$ are defined above;

(b) optionally oxidizing the resulting compound; and (c) optionally deprotecting the hydroxy-protected group.

12. The process according to claim 11, wherein Y and Z taken together is oxo, and X=O.

13. The process according to claim 12, wherein $R^2$ and $R^3$ each (—$CH_2CH_2$—O—$CH_2CH_2$—), and $R^P$ is benzoyl or hydrogen.

* * * * *

UNITED STATES PATENT AND TRADEMARK OFFICE
CERTIFICATE OF CORRECTION

PATENT NO. : 5,780,604
DATED : July 14, 1998
INVENTOR(S) : Or el al.

It is certified that error appears in the above-identified patent and that said Letters Patent is hereby corrected as shown below:

Column 26, line 25, change "$R^4$" to --$R^p$--.

Signed and Sealed this

Eighth Day of December, 1998

Attest:

BRUCE LEHMAN

Attesting Officer

Commissioner of Patents and Trademarks